United States Patent [19]

Rizzi et al.

[11] Patent Number: 5,183,922

[45] Date of Patent: Feb. 2, 1993

[54] PROCESS FOR THE OPTICAL RESOLUTION OF THREO-2-HYDROXY-3-(2'-AMINOPHENYL-THIO)-3-(4''-METHOXYPHENYL)-PROPIONIC ACID

[75] Inventors: Amleto Rizzi, Alte Ceccato; Gaetano Marchioro, Vicenza, both of Italy

[73] Assignee: FIS - Fabbrica Italiana Sintetici S.p.A., Vicenza, Italy

[21] Appl. No.: 615,686

[22] Filed: Nov. 19, 1990

[30] Foreign Application Priority Data

Nov. 23, 1989 [IT] Italy ............................. 22496 A/89

[51] Int. Cl.$^5$ ...................... C07C 319/28; C07B 57/00
[52] U.S. Cl. ........................................ 560/7; 562/401; 562/402; 562/431
[58] Field of Search ................... 562/401, 431; 560/17

[56] References Cited

U.S. PATENT DOCUMENTS 4,931,587  6/1990  Piselli ................................. 562/401
4,939,295  7/1990  Merli et al. ......................... 562/401

*Primary Examiner*—Jose G. Dees
*Assistant Examiner*—Vera C. Clarke
*Attorney, Agent, or Firm*—Diller, Ramik & Wight

[57] ABSTRACT

The present invention relates to a process for the separation of the enantiomers of threo-2-hydroxy-3-(2'-aminophenylthio)-3-(4''-methoxyphenyl)-propionic acid, which is an important intermediate in the synthesis of pharmacologically active compounds, by means of the direct crystallization of the relevant cyclohexylaminic salt.

According to a preferred form of practical embodiment of the present invention, the optically pure acid is recovered as the hydrochloride of the corresponding methyl ester.

5 Claims, No Drawings

PROCESS FOR THE OPTICAL RESOLUTION OF THREO-2-HYDROXY-3-(2'-AMINOPHENYLTHIO)-3-(4"-METHOXYPHENYL)-PROPIONIC ACID

The present invention relates to a new process for the resolution of the optical antipodes of threo-2-hydroxy-3-(2'-aminophenylthio)-3-(4"-methoxyphenyl)-propionic acid, having the formula (I):

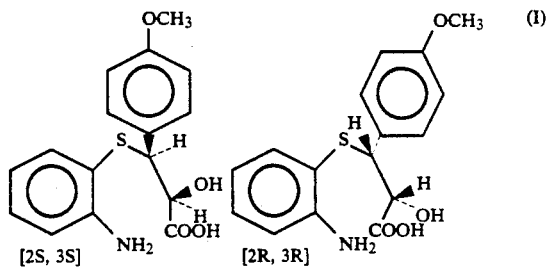

in which the hydrogen atoms bonded to the asymmetrical carbon atoms are in cis-position relatively to each other; as known, one of the optically active forms of this substance [i.e., the (+)-isomer] is an useful intermediate in the synthesis of a calcium-antagonist drug used in various forms of cardiac decompensation and insufficiency having the generic name of "diltiazem", or (+)-2-(4'-methoxyphenyl)-3-acetoxy-5-[2-(dimethylamino)-ethyl]-cis-2,3-dihydro-1,5-benzothiazepin-4-(5H)-one hydrochloride, represented by the formula (II):

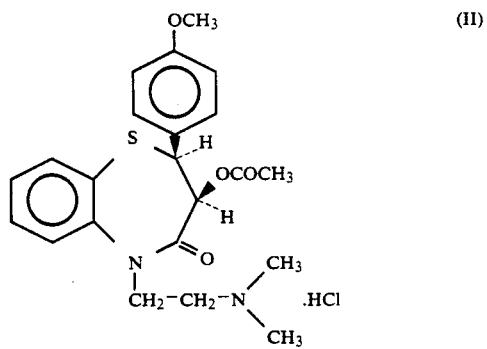

The separation of the racemic mixture of the acid of formula (I) into its optically active forms by means of the treatment of said mixture with optically pure bases, transformation of the enantiomers into a pair of mutually diastereoisomer salts, finally followed by a fractional distillation, is well-known.

Unfortunately, such a resolution method known from the prior art is affected by problems, such as an incomplete recovery, hence a low yield, of the enantiomers, and a high cost of the resolving agent, with the recovery and recycle thereof being hence necessary.

In order to overcome such problems, the present invention proposes a process for resolving the optical antipodes of threo-2-hydroxy-3-(2'-aminophenylthio)-3-(4"-methoxyphenyl)-propionic acid, having the formula (I):

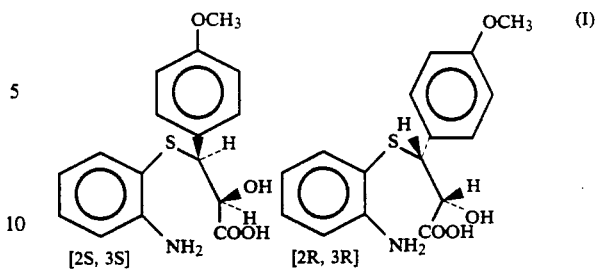

characterized in that said acid is salified with cyclohexylamine in a suitable solvent, and said optical antipodes are separated by means of the crystallization of their enantiomeric salts so formed.

The process according to the present invention carries out the optical resolution by means of the direct crystallization of the cyclohexylaminic salt of the dextro- and Levo- forms of said acid of formula (I) from polar organic solvents, such as methanol and dimethylformamide.

The salt formed by threo-2-hydroxy-3-(2'-aminophenylthio)-3-(4"-methoxyphenyl)-propionic acid with cyclohexylamine is a white, stable crystalline solid easily prepared by dissolving the acid and the amine in a solvent, at the boiling point of said solvent, and subsequent crystallization by cooling (yield 98%).

According to a form of practical embodiment of the present invention, the racemic salt is dissolved in dimethylformamide or methanol (in a from 5 to 40 times as large amount), in the presence of an excess of the pure salt in an amount comprised within the range of from 5 to 20% relatively to the amount of the racemic salt, at a temperature comprised within the range of from 60° to 80° C., and the whole is allowed to slowly crystallize at room temperature.

The optically pure salt used in order to supply the initial excess of one of the antipodes is prepared by means of the same modalities, by starting from one of the two optically active acids.

Usually, an amount of product is obtained which is approximately the double of the initially charged excess of pure isomer; its optical purity is comprised within the range of from 91 to 97%, with the pure product being obtained by means of a recrystallization. The cycle is then continued by adding to the resulting mother liquors an amount of racemic salt equal to the filtered off amount of pure isomer. The process is continued by repeatedly carrying out the above cycle, with the one enantiomer and then the other enantiomer being alternatively obtained.

According to the present invention, it was found that (+)-threo-2-hydroxy-3-(2'-aminophenylthio)-3-(4"-methoxyphenyl)-propionic acid forms with cyclohexylamine a salt endowed with ideal physical and chemical characteristics, which enable the separation of the enantiomers to be carried out by direct crystallization; in fact, this salt forms, even from a racemic solution, crystals either all constituted by (+)-molecules, or all constituted by (−)-molecules; and moreover, it shows a discrete tendency to form supersaturated solutions, making it possible for the mechanical separation of the enantiomers to be accomplished by unbalancing the racemic mixture used as the raw material, and seeding with the proper enantiomer.

As compared to the resolution process known from the prior art, which has resort to the use of optically active bases, the process according to the present invention offers the advantage that the charged amount of enantiomer (also including the not interesting isomer) is recovered to a practically complete extent in optically pure form, and that a base with a rather low cost is used, with the problems deriving from the recovery and recycle at the industrial level of the resolving agent being thereby overcome.

According to a further form of practical embodiment of the present invention, the process consists in the recovery of the acids of formula (I) from their salts with (either chiral or non-chiral) organic bases as methylester hydrochlorides, which can be obtained by treating the corresponding salt with hydrogen chloride gas in methanol under refluxing conditions.

These compounds are stable, they can be easily crystallized and dried, an enable more than 95% of the corresponding optically active acid to be recovered.

The direct conversion of the salt into the ester makes it possible a pure product to be obtained, with a practically theoretical yield.

Furthermore the ester, as disclosed in Applicants' co-pending patent application Ser. No. 07/615,687, filed Nov. 19, 1990, now U.S. Pat. No. 5,128,468, is very easily cyclised in order to produce the corresponding 1,5-benzothiazepinic derivative, which is the desired end product.

The following non-limiting Examples and preparations illustrate the operating conditions of the process of the present invention:

SYNTHESIS OF THE SALTS

Preparation 1

Salt of threo-2-hydroxy-3-(2'-aminophenylthio)-3-(4''-methoxyphenyl)-propionic acid with cyclohexylamine Under refluxing conditions, 130 g (402 mmol) of threo-2-hydroxy-3-(2'-aminophenylthio)-3-(4''-methoxyphenyl)-propionic acid and 41.4 g (417 mmol) of cyclohexylamine are dissolved in 1 liter of methanol.

The solution is cooled down to 0° C. and is kept with stirring for 2 hours.

167 g of a soft solid of white colour is obtained.
Yield 98%
Melting point 185°–186° C.

PREPARATION 2

Salt of (+)-threo-2-hydroxy-3-(2'-aminophenylthio)-3-(4''-methoxyphenyl)-propionic acid with cyclohexylamine Under refluxing conditions, 31.9 g (100 mmol) of (+)-threo-2-hydroxy-3-(2'-aminophenylthio)-3-(4''-methoxyphenyl)-propionic acid and 10.4 g (105 mmol) of cyclohexylamine are dissolved in 250 ml of methanol.

The solution is cooled down to 0° C. and is kept with stirring for 2 hours.

41.0 g of a soft solid of white colour is obtained.
Yield 98%
Melting point 186°–187° C.
$[\alpha]_D^{20} = +394°$ (C=1%, methanol).

EXAMPLE 1

Resolution of threo-2-hydroxy-3-(2'-aminophenylthio)-3-(4''-methoxyphenyl)-propionic acid 44.0 g (105 mmol) of the salt of threo-2-hydroxy-3-(2'-aminophenylthio)-3-(4''-methoxyphenyl)-propionic acid with cyclohexylamine and 6.0 g (14 mmol) of the salt of (+)-threo-2-hydroxy-3-(2'-aminophenylthio)-3-(4''-methoxyphenyl)-propionic acid with cyclohexylamine are dissolved in 400 ml of dimethylformamide at the temperature of 75° C.

The mixture is stirred for a few minutes until a clear solution is obtained, then the solution is cooled down to 30° C. a crystal seed of (+)-salt is added, and the temperature is further reduced down to 20° C.

The mixture is stirred for approximately 2 hours, and is then filtered. The filter cake is washed with a small volume of isopropanol.

A product is obtained, the dry weight of which is of 12.0 g.
Melting point 186°–187° C.
$[\alpha]_D^{20} = +370°$ (C=1%, methanol).

The yield is not calculated, in that the mother liquors are continuously recycled and the product losses are only those caused by the mechanical losses of solution.

EXAMPLE 2

Resolution of threo-2-hydroxy-3-(2'-aminophenylthio)-3-(4-methoxyphenyl)-propionic acid 41.9 g (100 mmol) of the salt of threo-2-hydroxy-3-(2'-aminophenylthio)-3-(4''-methoxyphenyl)-propionic acid with cyclohexylamine and 4.2 g (10 mmol) of the salt of (+)-threo-2-hydroxy-3-(2'-aminophenylthio)-3-(4''-methoxyphenyl)-propionic acid with cyclohexylamine are dissolved in 1300 ml of methanol at the solvent boiling temperature.

The mixture is cooled, with its temperature being decreased down to 10°–12° C. The mixture is then kept with stirring for 1 hour.

The mixture is filtered, the filter cake is washed with a small volume of cold methanol and 8.4 g of a soft product of white colour is obtained.
Melting point 186°–187° C.
$[\alpha]_D^{20} = +374°$ (C=1%, methanol).

EXAMPLE 3

The mother liquors resulting from Example 1 are admixed with 12 g of the salt of threo-2-hydroxy-3-(2'-amino-phenylthio)-3-(4''-methoxyphenyl)-propionic acid with cyclohexylamine.

The mixture is heated up to 75° C., is stirred for a few minutes until a clear solution is obtained, then the solution is cooled to 30° C. and a crystal seed of (−) salt is added, and the temperature is further reduced down to 20° C.

The mixture is stirred at this temperature for approximately 2 hours, and is then filtered.

The precipitate is washed with a small volume of isopropanol.

A crystalline product is obtained, the dry weight of which is of 12 g.
Melting point 186°–187° C.
$[\alpha]_D^{20} = -370°$ (C=1%, methanol).

EXAMPLE 4

The mother liquors of the preceding Example are admixed with a further 12 g of racemic salt.

The above disclosed procedure is repeated, with the crystallization being triggered at 30° C. with (+)-salt.

The system is thus reported back to the same conditions as disclosed in Example 1, with similar results being obtained.

EXAMPLE 5

The mother liquors resulting from Example 2 are admixed with 8.4 g of the racemic salt of threo-2-hydroxy-3-(2'-amino-phenylthio)-3-(4"-methoxyphenyl)-propionic acid with cyclohexylamine.

The process disclosed in Example 2 is repeated, and 8.4 g of (−)-salt is obtained.

The mother liquors are recycled in the same way.

EXAMPLE 6

Methyl (+)-threo-2-hydroxy-3-(2'-amino-phenylthio)-3-(4"-methoxyphenyl)-propionate hydrochloride Hydrogen chloride gas is bubbled through a mixture of 83.7 g (200 mmol) of the salt of (+)-threo-2-hydroxy-3-(2'-amino-phenylthio)-3-(4"-methoxyphenyl)-propionic acid with cyclohexylamine in 300 ml of methanol, and the mixture is then heated up to its boiling temperature.

The reaction mixture is kept at its boiling temperature and when the hydrochloride salt begins to precipitate, the flow of hydrogen chloride is discontinued, the mixture is refluxed for a further 30 minutes, then 100 ml of methanol is distilled off.

The reaction mixture is cooled down to −10° C. and after filtration and drying 71.8 g of a crystalline solid of white colour is obtained.

Yield 97%.
Melting point 196°–198° C.
$[\alpha]_D^{20} = 35.0°$ (C=0.635, methanol).

We claim:

1. Process for resolving the optical antipodes of threo-2-hydroxy-3-(2'-aminophenylthio)-3-(4"-methoxyphenyl)-propionic acid, having the formula (I):

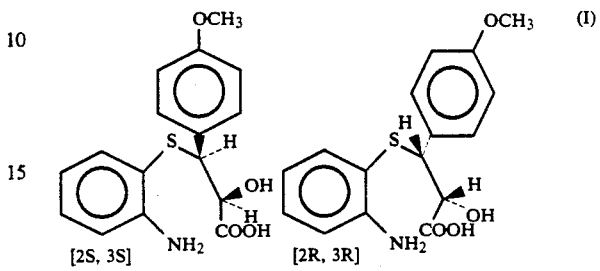

characterized in that said acid is salified with cyclohexylamine in a polar organic solvent, and said optical antipodes are separated by means of the crystallization of their so formed enantiomeric salts.

2. Process according to claim 1, wherein an excess of the same enantiomeric salt which is recovered during said process is added in an optically pure form to the solution of said enantiomeric salts before said crystallization.

3. Process according to claim 1, wherein said polar organic solvent is selected from the group consisting of methanol and dimethylformamide.

4. Process according to claim 3, wherein said solvent is methanol.

5. Process according to claim 4, comprising the step of adding hydrogen chloride gas to said acid as it is being salified such that the enantiomeric salts being formed comprise the corresponding methylester hydrochloride.

* * * * *